(12) United States Patent
Puryear et al.

(10) Patent No.: US 10,575,876 B2
(45) Date of Patent: Mar. 3, 2020

(54) SPINAL STABILIZATION ASSEMBLIES WITH BONE HOOKS

(71) Applicant: K2M, Inc., Leesburg, VA (US)

(72) Inventors: Aki Puryear, St. Louis, MO (US); Brandon Moore, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 160 days.

(21) Appl. No.: 15/492,125

(22) Filed: Apr. 20, 2017

(65) Prior Publication Data

US 2017/0303970 A1 Oct. 26, 2017

Related U.S. Application Data

(60) Provisional application No. 62/325,112, filed on Apr. 20, 2016.

(51) Int. Cl.
*A61B 17/70* (2006.01)
*A61B 17/56* (2006.01)

(52) U.S. Cl.
CPC ...... *A61B 17/7032* (2013.01); *A61B 17/7047* (2013.01); *A61B 2017/564* (2013.01)

(58) Field of Classification Search
CPC ............ A61B 17/7047; A61B 17/7032; A61B 17/7056; A61B 17/7049; A61B 17/7041; A61B 17/7037; A61B 17/7001; A61B 17/7035
See application file for complete search history.

(56) References Cited

U.S. PATENT DOCUMENTS

| | | | |
|---|---|---|---|
| 1,404,248 A | 5/1889 | Bartlett | |
| 2,752,074 A | 2/1904 | Jackson | |
| 4,047,523 A | 9/1977 | Hall | |
| 4,257,409 A | 3/1981 | Bacal et al. | |
| 4,269,178 A | 5/1981 | Keene | |
| 4,274,401 A * | 6/1981 | Miskew | A61B 17/7004 606/256 |
| 4,347,845 A | 9/1982 | Mayfield | |
| 4,369,770 A | 1/1983 | Bacal et al. | |
| 4,382,438 A | 5/1983 | Jacobs | |
| 4,404,967 A | 9/1983 | Bacal et al. | |
| 4,409,968 A | 10/1983 | Drummond | |
| 4,411,259 A | 10/1983 | Drummond | |
| 4,422,451 A | 12/1983 | Kalamchi | |

(Continued)

FOREIGN PATENT DOCUMENTS

| | | |
|---|---|---|
| WO | 8001137 A1 | 6/1980 |
| WO | 9310728 A1 | 6/1993 |

(Continued)

*Primary Examiner* — Lynnsy M Summitt
(74) *Attorney, Agent, or Firm* — Lerner, David, Littenberg, Krumholz & Mentlik, LLP

(57) ABSTRACT

A spinal stabilization assembly includes a first hook assembly, a second hook assembly, and a connector member. The first hook assembly has a receiver and a hook member that extends from the receiver. The receiver defines a rod-receiving slot configured to receive a spinal rod. The hook member defines an aperture and includes a hook. The aperture is supported between the rod-receiving slot and the hook. The connector member is secured to the second hook assembly and receivable in the aperture of the first hook assembly to couple the first and second hook assemblies together.

13 Claims, 20 Drawing Sheets

(56) References Cited

U.S. PATENT DOCUMENTS

| | | | |
|---|---|---|---|
| 4,433,676 A | 2/1984 | Bobechko | |
| 4,567,884 A | 2/1986 | Edwards | |
| 4,641,636 A | 2/1987 | Cotrel | |
| 4,815,453 A | 3/1989 | Cotrel | |
| 4,854,304 A | 8/1989 | Zielke | |
| 5,005,562 A | 4/1991 | Cotrel | |
| 5,007,909 A * | 4/1991 | Rogozinski | A61B 17/7041 606/277 |
| 5,010,879 A | 4/1991 | Moriya et al. | |
| 5,242,445 A | 9/1993 | Ashman | |
| 5,246,442 A | 9/1993 | Ashman et al. | |
| 5,261,913 A * | 11/1993 | Marnay | A61B 17/7052 403/290 |
| 5,263,954 A | 11/1993 | Schlapfer et al. | |
| 5,267,999 A * | 12/1993 | Olerud | A61B 17/7047 606/277 |
| 5,281,222 A | 1/1994 | Allard et al. | |
| 5,282,801 A | 2/1994 | Sherman | |
| 5,306,275 A | 4/1994 | Bryan | |
| 5,330,472 A | 7/1994 | Metz-Stavenhagen | |
| 5,344,422 A | 9/1994 | Frigg | |
| 5,360,429 A * | 11/1994 | Jeanson | A61B 17/7002 606/250 |
| 5,374,267 A | 12/1994 | Siegal | |
| 5,380,326 A * | 1/1995 | Lin | A61B 17/7032 403/13 |
| 5,423,818 A | 6/1995 | Van Hoeck et al. | |
| 5,437,669 A * | 8/1995 | Yuan | A61B 17/704 606/264 |
| 5,437,670 A | 8/1995 | Sherman et al. | |
| 5,454,812 A | 10/1995 | Lin | |
| 5,476,462 A | 12/1995 | Allard et al. | |
| 5,496,321 A | 3/1996 | Puno et al. | |
| 5,498,262 A | 3/1996 | Bryan | |
| 5,507,745 A | 4/1996 | Logroscino et al. | |
| 5,514,132 A | 5/1996 | Csernatony et al. | |
| 5,527,314 A | 6/1996 | Brumfield et al. | |
| 5,534,001 A | 7/1996 | Schlapfer et al. | |
| 5,534,002 A | 7/1996 | Brumfield et al. | |
| 5,542,946 A | 8/1996 | Logroscino et al. | |
| 5,545,165 A | 8/1996 | Biedermann et al. | |
| 5,545,167 A | 8/1996 | Lin | |
| 5,562,662 A | 10/1996 | Brumfield et al. | |
| 5,575,792 A | 11/1996 | Errico et al. | |
| 5,578,033 A * | 11/1996 | Errico | A61B 17/7037 606/276 |
| 5,582,612 A * | 12/1996 | Lin | A61B 17/7044 606/250 |
| 5,584,832 A | 12/1996 | Schlapfer | |
| 5,601,552 A | 2/1997 | Cotrel | |
| 5,609,592 A | 3/1997 | Brumfield et al. | |
| 5,609,593 A * | 3/1997 | Errico | A61B 17/7037 606/266 |
| 5,620,444 A | 4/1997 | Assaker | |
| 5,624,441 A | 4/1997 | Sherman et al. | |
| 5,630,816 A | 5/1997 | Kambin | |
| 5,676,665 A | 10/1997 | Bryan | |
| 5,683,392 A * | 11/1997 | Richelsoph | A61B 17/7037 606/272 |
| 5,688,272 A | 11/1997 | Montague et al. | |
| 5,688,273 A | 11/1997 | Errico et al. | |
| 5,688,274 A | 11/1997 | Errico et al. | |
| 5,709,685 A | 1/1998 | Dombrowski et al. | |
| 5,716,356 A | 2/1998 | Biedermann et al. | |
| 5,725,527 A | 3/1998 | Biedermann et al. | |
| 5,741,254 A | 4/1998 | Henry et al. | |
| 5,743,911 A | 4/1998 | Cotrel | |
| 5,810,818 A * | 9/1998 | Errico | A61B 17/7056 606/276 |
| D404,248 S | 1/1999 | Blaise | |
| 5,899,903 A | 5/1999 | Cotrel | |
| 5,928,231 A | 7/1999 | Klein et al. | |
| 5,928,232 A * | 7/1999 | Howland | A61B 17/7001 606/276 |
| 5,961,517 A | 10/1999 | Biedermann et al. | |
| 5,980,521 A | 11/1999 | Montague et al. | |
| 5,989,250 A | 11/1999 | Wagner et al. | |
| 6,010,503 A * | 1/2000 | Richelsoph | A61B 17/7032 606/278 |
| 6,015,409 A | 1/2000 | Jackson | |
| 6,077,263 A * | 6/2000 | Ameil | A61B 17/7032 606/276 |
| 6,086,588 A | 7/2000 | Ameil et al. | |
| 6,096,039 A | 8/2000 | Stoltenberg et al. | |
| 6,117,136 A | 9/2000 | Von Strempel | |
| 6,132,430 A | 10/2000 | Wagner | |
| 6,136,000 A * | 10/2000 | Louis | A61B 17/7047 606/250 |
| 6,179,838 B1 | 1/2001 | Fiz | |
| 6,387,097 B1 * | 5/2002 | Alby | A61B 17/7032 606/277 |
| 6,416,515 B1 | 7/2002 | Wagner | |
| 6,562,040 B1 | 5/2003 | Wagner | |
| 6,589,243 B1 * | 7/2003 | Viart | A61B 17/7047 606/250 |
| 6,595,992 B1 | 7/2003 | Wagner et al. | |
| 6,610,063 B2 | 8/2003 | Kumar et al. | |
| 6,613,050 B1 | 9/2003 | Wagner et al. | |
| 6,689,132 B2 | 2/2004 | Biscup | |
| 6,695,843 B2 | 2/2004 | Biedermann et al. | |
| 6,802,845 B2 | 10/2004 | Shirado et al. | |
| 6,804,101 B2 | 10/2004 | Tignor et al. | |
| 6,858,029 B2 | 2/2005 | Yeh | |
| 6,860,884 B2 | 3/2005 | Shirado et al. | |
| 6,911,030 B1 | 6/2005 | Vanacker et al. | |
| 6,932,817 B2 | 8/2005 | Baynham et al. | |
| 7,011,659 B2 | 3/2006 | Lewis et al. | |
| 7,033,358 B2 | 4/2006 | Taylor et al. | |
| 7,118,571 B2 | 10/2006 | Kumar et al. | |
| 7,338,490 B2 | 3/2008 | Ogilvie et al. | |
| 7,485,133 B2 | 2/2009 | Cannon et al. | |
| 7,569,070 B2 | 8/2009 | Suzuki et al. | |
| 7,572,278 B2 | 8/2009 | Suzuki et al. | |
| 7,678,114 B2 | 3/2010 | Heinz et al. | |
| 7,695,497 B2 | 4/2010 | Cordaro et al. | |
| 7,717,941 B2 | 5/2010 | Petit | |
| 7,901,436 B2 | 3/2011 | Baccelli | |
| 7,959,655 B2 | 6/2011 | Kawakami et al. | |
| 7,988,694 B2 * | 8/2011 | Barrus | A61B 17/7032 606/246 |
| 8,029,543 B2 | 10/2011 | Young et al. | |
| 8,043,337 B2 | 10/2011 | Klyce et al. | |
| 8,066,743 B2 | 11/2011 | Young et al. | |
| 8,083,780 B2 | 12/2011 | McClellan, III et al. | |
| 8,133,263 B2 | 3/2012 | Lewis et al. | |
| 8,162,991 B2 * | 4/2012 | Strauss | A61B 17/7037 606/269 |
| 8,172,882 B2 | 5/2012 | Klyce et al. | |
| 8,177,823 B2 | 5/2012 | Lake et al. | |
| 8,202,299 B2 | 6/2012 | Wang et al. | |
| 8,221,470 B2 | 7/2012 | Kumar et al. | |
| 8,226,689 B2 | 7/2012 | Jones et al. | |
| 8,414,617 B2 | 4/2013 | Young et al. | |
| 8,425,563 B2 | 4/2013 | Firkins | |
| 8,512,380 B2 | 8/2013 | Farris et al. | |
| 8,551,146 B2 | 10/2013 | Kumar et al. | |
| 8,715,323 B2 | 5/2014 | Ballard et al. | |
| 8,721,688 B1 | 5/2014 | Wang et al. | |
| 8,814,919 B2 * | 8/2014 | Barrus | A61B 17/7037 606/266 |
| 8,870,926 B2 | 10/2014 | Kumar et al. | |
| 8,882,803 B2 | 11/2014 | Iott et al. | |
| 8,882,808 B2 | 11/2014 | Baccelli | |
| 8,926,673 B2 | 1/2015 | Clement et al. | |
| 8,956,392 B2 | 2/2015 | Khatchadourian et al. | |
| 8,974,500 B2 | 3/2015 | Khatchadourian et al. | |
| 2003/0109882 A1* | 6/2003 | Shirado | A61B 17/7032 606/324 |
| 2003/0187437 A1 | 10/2003 | Ginsburg | |
| 2004/0064140 A1* | 4/2004 | Taylor | A61B 17/7037 606/277 |

(56) References Cited

U.S. PATENT DOCUMENTS

| | | | |
|---|---|---|---|
| 2004/0186473 A1* | 9/2004 | Cournoyer | A61B 17/7032 606/266 |
| 2004/0260285 A1* | 12/2004 | Steib | A61B 17/7032 606/276 |
| 2005/0038429 A1 | 2/2005 | Elsebaie | |
| 2005/0080414 A1 | 4/2005 | Keyer et al. | |
| 2006/0084990 A1* | 4/2006 | Gournay | A61B 17/7007 606/276 |
| 2006/0276792 A1* | 12/2006 | Ensign | A61B 17/7032 606/264 |
| 2006/0293660 A1 | 12/2006 | Lewis et al. | |
| 2007/0055243 A1 | 3/2007 | Kumar et al. | |
| 2007/0161990 A1 | 7/2007 | Hillyard et al. | |
| 2007/0173819 A1 | 7/2007 | Sandlin | |
| 2007/0233089 A1 | 10/2007 | DiPoto et al. | |
| 2007/0270835 A1* | 11/2007 | Wisnewski | A61B 17/7032 606/86 A |
| 2007/0288013 A1 | 12/2007 | Sanders | |
| 2008/0058808 A1 | 3/2008 | Klyce et al. | |
| 2008/0114401 A1* | 5/2008 | Liu | A61B 17/7044 606/276 |
| 2008/0140124 A1 | 6/2008 | Jeon et al. | |
| 2008/0147121 A1* | 6/2008 | Justis | A61B 17/7001 606/246 |
| 2008/0262547 A1 | 10/2008 | Lewis et al. | |
| 2010/0069961 A1 | 3/2010 | DiPoto et al. | |
| 2010/0131020 A1 | 5/2010 | Heinz et al. | |
| 2010/0222822 A1* | 9/2010 | Farris | A61B 17/7004 606/264 |
| 2010/0234892 A1* | 9/2010 | Mazda | A61B 17/705 606/276 |
| 2011/0015679 A1* | 1/2011 | Fiere | A61B 17/7001 606/276 |
| 2012/0158065 A1* | 6/2012 | Jouve | A61B 17/7001 606/276 |
| 2013/0144342 A1* | 6/2013 | Strauss | A61B 17/701 606/261 |
| 2013/0184762 A1 | 7/2013 | Harper et al. | |
| 2013/0231704 A1 | 9/2013 | Larroque-Lahitette | |
| 2013/0261668 A1 | 10/2013 | Douget et al. | |
| 2013/0274808 A1* | 10/2013 | Larroque-Lahitette | A61B 17/7005 606/278 |
| 2013/0304129 A1 | 11/2013 | Hawkins et al. | |
| 2014/0188173 A1 | 7/2014 | Mishra et al. | |
| 2014/0200617 A1 | 7/2014 | Farris et al. | |
| 2014/0222074 A1 | 8/2014 | Rathbun et al. | |
| 2014/0277152 A1 | 9/2014 | Hammer et al. | |
| 2014/0277155 A1* | 9/2014 | Barrus | A61B 17/7056 606/276 |
| 2014/0303675 A1 | 10/2014 | Mishra | |
| 2014/0343612 A1* | 11/2014 | Rezach | A61B 17/7032 606/276 |
| 2015/0012043 A1 | 1/2015 | Kumar et al. | |
| 2015/0025584 A1 | 1/2015 | Iott et al. | |
| 2015/0066090 A1 | 3/2015 | Baccelli | |
| 2015/0112391 A1 | 4/2015 | Legallois et al. | |
| 2015/0230828 A1* | 8/2015 | Barrus | A61B 17/7032 606/276 |
| 2016/0015430 A1* | 1/2016 | Buttermann | A61B 17/7032 606/276 |
| 2016/0183981 A1* | 6/2016 | Schlaepfer | A61B 17/7055 606/324 |
| 2017/0181772 A1* | 6/2017 | Buttermann | A61B 17/7032 |

FOREIGN PATENT DOCUMENTS

| | | |
|---|---|---|
| WO | 9312737 A1 | 7/1993 |
| WO | 9408527 A1 | 4/1994 |
| WO | 9415554 A1 | 7/1994 |
| WO | 9416635 A1 | 8/1994 |
| WO | 9418917 A1 | 9/1994 |
| WO | 9421186 A1 | 9/1994 |
| WO | 9423660 A1 | 10/1994 |
| WO | 9426190 A1 | 11/1994 |
| WO | 9505126 A1 | 2/1995 |
| WO | 9506440 A1 | 3/1995 |
| WO | 9513755 A1 | 5/1995 |
| WO | 9517863 A1 | 7/1995 |
| WO | 9522291 A1 | 8/1995 |
| WO | 9525473 A1 | 9/1995 |
| WO | 9532677 A1 | 12/1995 |
| WO | 9602198 A1 | 2/1996 |
| WO | 9636291 A1 | 11/1996 |
| WO | 9743974 A1 | 11/1997 |
| WO | 9817188 A1 | 4/1998 |
| WO | 9849960 A1 | 11/1998 |
| WO | 9852483 A1 | 11/1998 |
| WO | 9904716 A1 | 2/1999 |
| WO | 9918874 A1 | 4/1999 |
| WO | 200101873 A1 | 1/2001 |
| WO | 200238060 A1 | 5/2002 |
| WO | 200353264 A1 | 7/2003 |
| WO | 200365912 A2 | 8/2003 |
| WO | 200396917 A1 | 11/2003 |
| WO | 200399148 A2 | 12/2003 |
| WO | 200424011 A1 | 3/2004 |
| WO | 200439268 A1 | 5/2004 |
| WO | 200439269 A2 | 5/2004 |
| WO | 200482464 A2 | 9/2004 |
| WO | 2004112626 A2 | 12/2004 |
| WO | 200523126 A1 | 3/2005 |
| WO | 200537066 A2 | 4/2005 |
| WO | 200541794 A1 | 5/2005 |
| WO | 200619678 A1 | 2/2006 |
| WO | 200705561 A2 | 1/2007 |
| WO | 200738076 A1 | 4/2007 |
| WO | 200773537 A1 | 6/2007 |
| WO | 200782019 A2 | 7/2007 |
| WO | 2007111795 A1 | 10/2007 |
| WO | 2007146928 A2 | 12/2007 |
| WO | 200891266 A1 | 7/2008 |
| WO | 2008109229 A2 | 9/2008 |
| WO | 2009117610 A2 | 9/2009 |
| WO | 2009118692 A1 | 10/2009 |
| WO | 201043496 A1 | 4/2010 |
| WO | 201062718 A1 | 6/2010 |
| WO | 2010114880 A1 | 10/2010 |
| WO | 2010150140 A1 | 12/2010 |
| WO | 201262879 A1 | 5/2012 |
| WO | 201272413 A1 | 6/2012 |
| WO | 201284654 A1 | 6/2012 |
| WO | 2013109812 A1 | 7/2013 |
| WO | 201409338 A1 | 1/2014 |
| WO | 2014106234 A1 | 7/2014 |
| WO | 2014151037 A1 | 9/2014 |

* cited by examiner

SPINAL STABILIZATION ASSEMBLIES WITH BONE HOOKS

CROSS-REFERENCE TO RELATED APPLICATIONS

This application claims priority to, and the benefit of, U.S. Provisional Patent Application Ser. No. 62/325,112, filed Apr. 20, 2016, the entire contents of which are hereby incorporated by reference.

TECHNICAL FIELD

The present disclosure relates to spinal surgery. More specifically, the present disclosure relates to spinal stabilization assemblies with bone hooks.

BACKGROUND

The spinal column is a complex system of bones and connective tissues that provide support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury which restrict the range of motion of the spine or interfere with important elements of the nervous system. The problems include, but are not limited to scoliosis, kyphosis, excessive lordosis, spondylolisthesis, slipped or ruptured discs, degenerative disc disease, vertebral body fracture, and tumors. Persons suffering from any of the above conditions may experience extreme or debilitating pain and diminished nerve function. These conditions and their treatments can be further complicated if the patient is suffering from osteoporosis, or bone tissue thinning and loss of bone density.

Spinal fixation apparatuses are widely employed in surgical procedures for correcting spinal injuries and diseases. When the disc has degenerated to the point of requiring removal, there are a variety of interbody implants that are utilized to take the place of the disc. These include polyetheretherketone ("PEEK") interbody spacers, metal cages, and cadaver and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws, hooks, and others. Bone hook systems, for example, can be utilized to create a clamping effect on bone in order to facilitate stabilization of bone.

Accordingly, a continuing need exists to provide an effective, efficient, and reliable bone hook system that can be utilized for stabilizing bone during a spinal procedure.

SUMMARY

Accordingly, one aspect of the present disclosure is directed to a spinal stabilization assembly comprising a first hook assembly, a second hook assembly and a connector member.

The first hook assembly has a receiver and a hook member that extends from the receiver. The hook member may include a head supported on a trailing end thereof. The receiver defines a rod-receiving slot configured to receive a spinal rod therein. The hook member defines an aperture and includes a hook. The aperture is positioned between the rod-receiving slot and the hook.

The connector member is secured to the second hook assembly and is at least partially receivable in the aperture of the first hook assembly to couple the first and second hook assemblies together.

In some embodiments, at least a portion of the connector member may be slidably received in the aperture to selectively position the first and second hook assemblies between first and second positions. In the second position, the first and second hook assemblies may be closer to one another than in the first position.

In some embodiments, the first hook assembly may include a set screw receivable within the receiver of the first hook assembly. The set screw may be selectively positionable in contact with the connector member to fix a distance between the first and second hook assemblies.

In certain embodiments, the receiver of the first hook assembly may include an outer housing and an inner housing supported within the outer housing. The inner and outer housings may define the rod-receiving slot. The inner and outer housings may be supported in a taper lock arrangement to selectively secure the spinal rod within the rod-receiving slot upon relative movement between the inner and outer housings. The inner housing may be supported on the head of the hook member of the first hook assembly. The hook member of the first hook assembly may include a coupling member supported between the head and the hook of the hook member. The coupling member may define the aperture therethrough.

In some embodiments, the second hook assembly may include a hook. The hooks of the first and second assemblies may be disposed in mirrored relation with one another and in parallel relation with the connector member.

In certain embodiments, the second hook assembly may be supported entirely beneath the spinal rod while the spinal rod is secured within the rod-receiving slot of the first hook assembly.

In some embodiments, the receiver and the hook member of the first hook assembly may be polyaxially movable relative to one another.

According to yet another aspect of the present disclosure, a spinal stabilization assembly comprises a spinal rod, a first hook assembly, a second hook assembly, and a connector member.

The first hook assembly has a receiver and a hook member that extends from the receiver. The receiver defines a rod-receiving slot configured to receive the spinal rod therein. The connector member extends between the first and second hook assemblies. The connector member is secured to the first assembly and selectively securable to the second hook assembly.

In some embodiments, the connector member may be slidably received through the first hook assembly.

In certain embodiments, the hook member of the first hook assembly may include a coupling member supported between the head and the hook of the hook member. The coupling member may define an aperture that is positioned to receive the connector member therethrough.

In some embodiments, the second hook assembly may include a hook member. The hook members of the first and second assemblies may be disposed in mirrored relation with one another and in parallel relation with the connector member.

According to still another aspect of the present disclosure, a method for stabilizing a spine is provided. The method includes securing a hook of a first hook assembly to a first spinal bone, securing a hook of second hook assembly to a second spinal bone, coupling a connector member of the second hook assembly to the first hook assembly, adjusting a distance between the first and second hook assemblies to manipulate the first and second spinal bones relative to one another, securing the connector member of the second hook assembly to the first hook assembly to fix a distance between the first and second hook assemblies, and mounting a spinal rod to a receiver of the first hook assembly.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Figure 1:
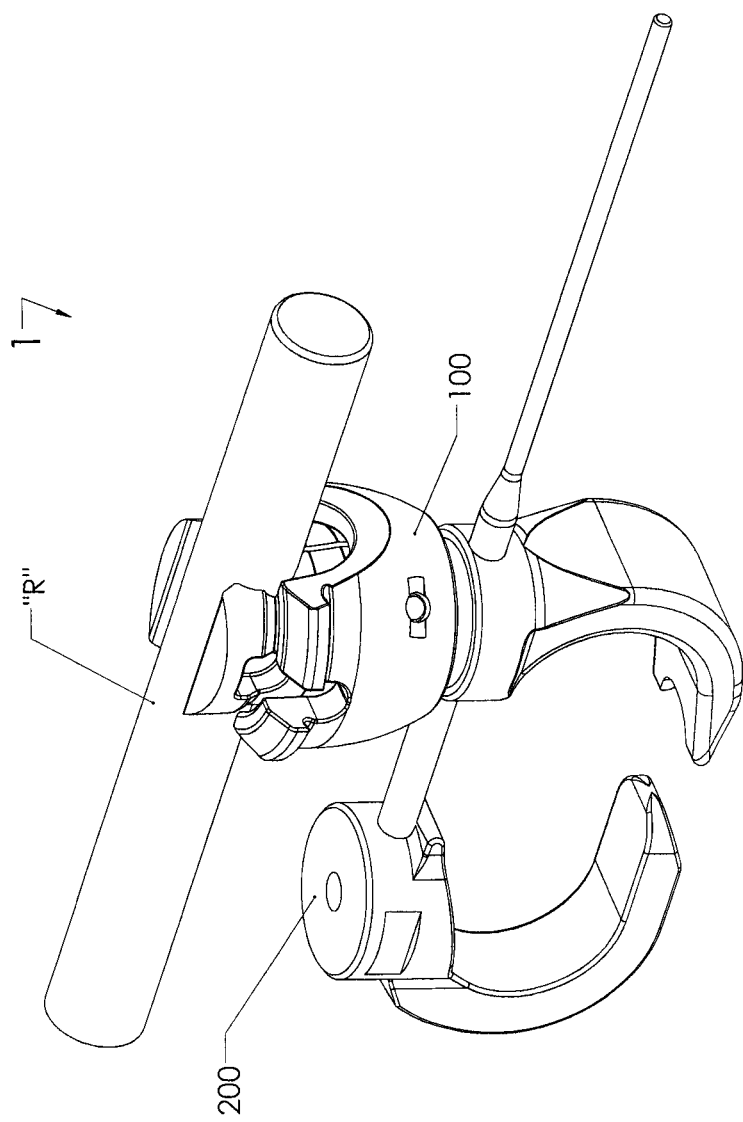
FIG. 1 is a perspective view of one embodiment of a spinal stabilization assembly in accordance with the principles of the present disclosure, the spinal stabilization assembly shown supporting a spinal rod.
Figure 2:
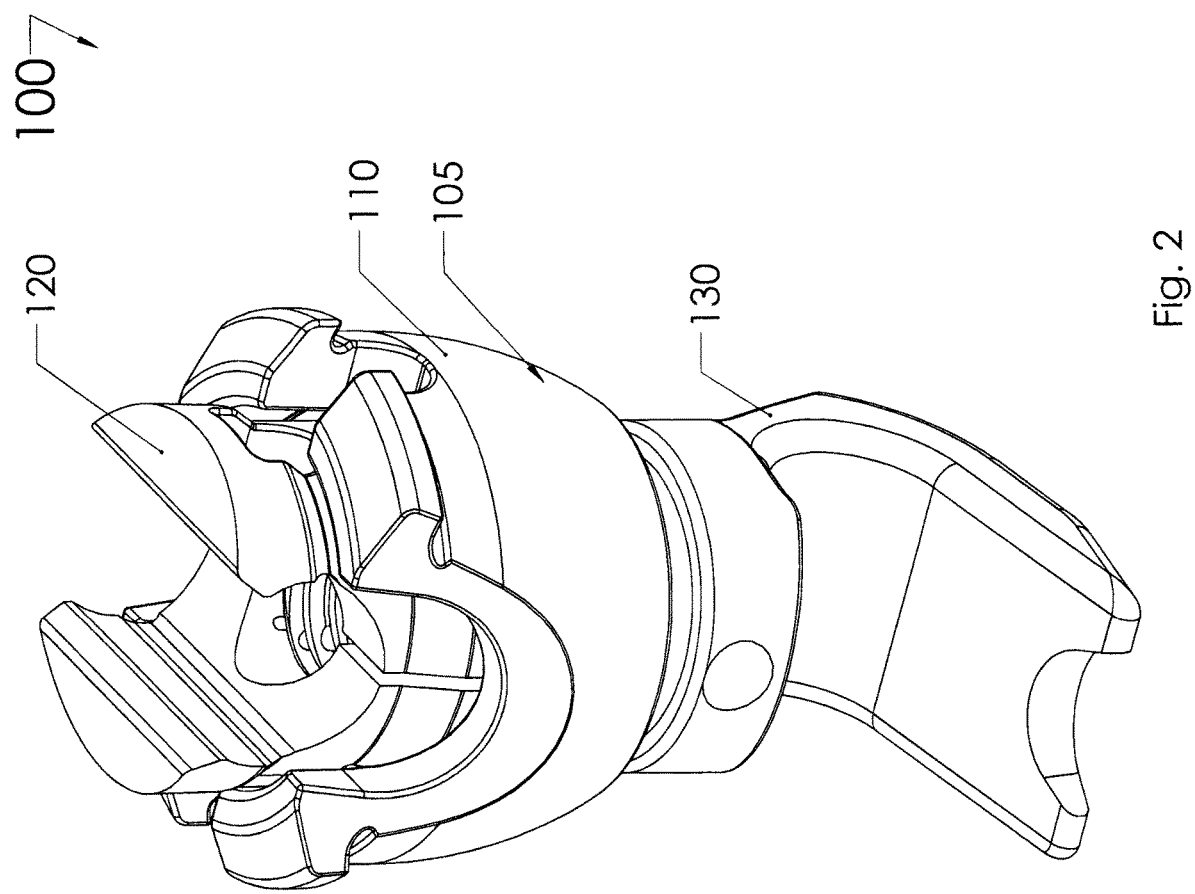
FIG. 2 is a front, perspective view of a first hook assembly of the spinal stabilization assembly of FIG. 1.
Figure 3:
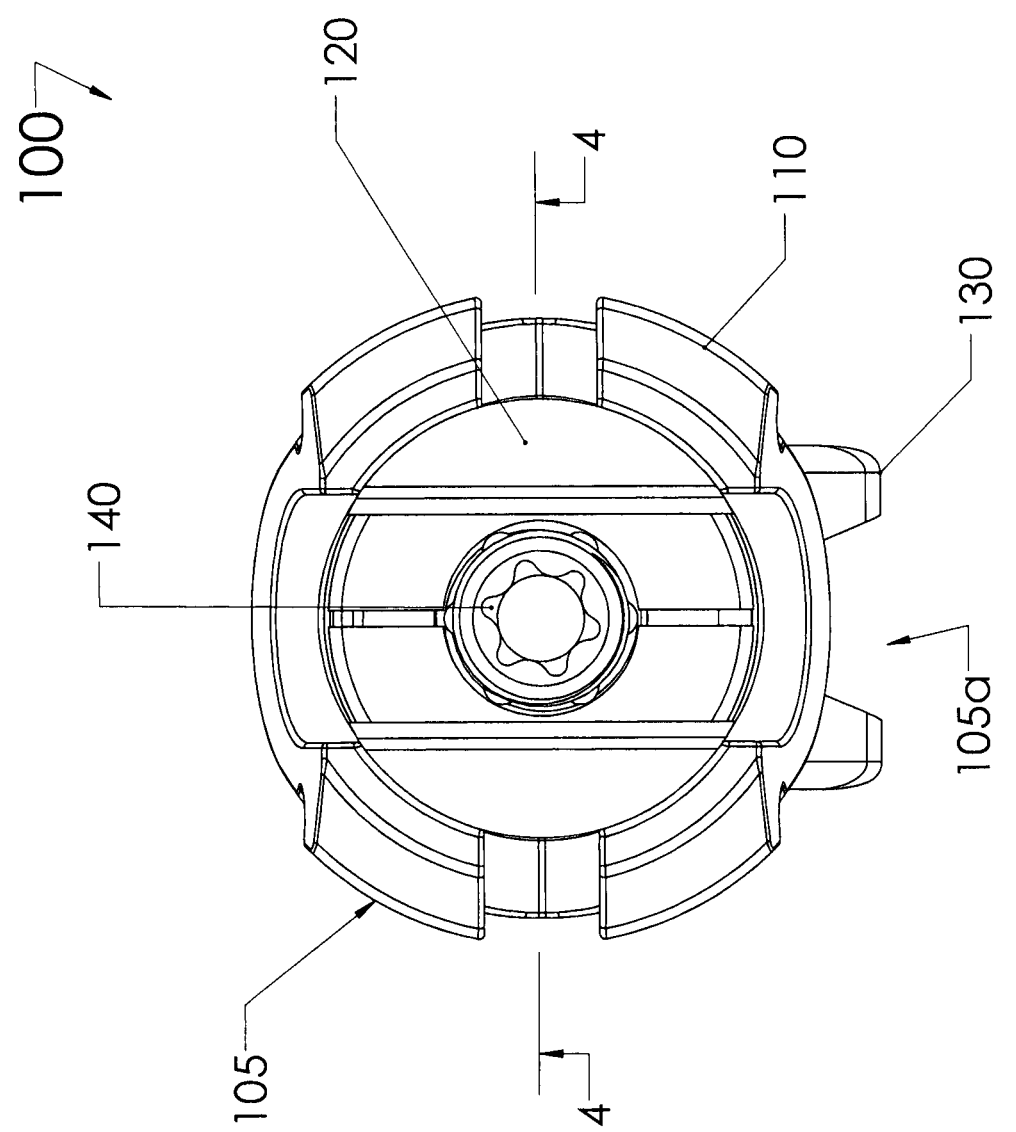
FIG. 3 is a top view of the first hook assembly of FIG. 2.
Figure 4:
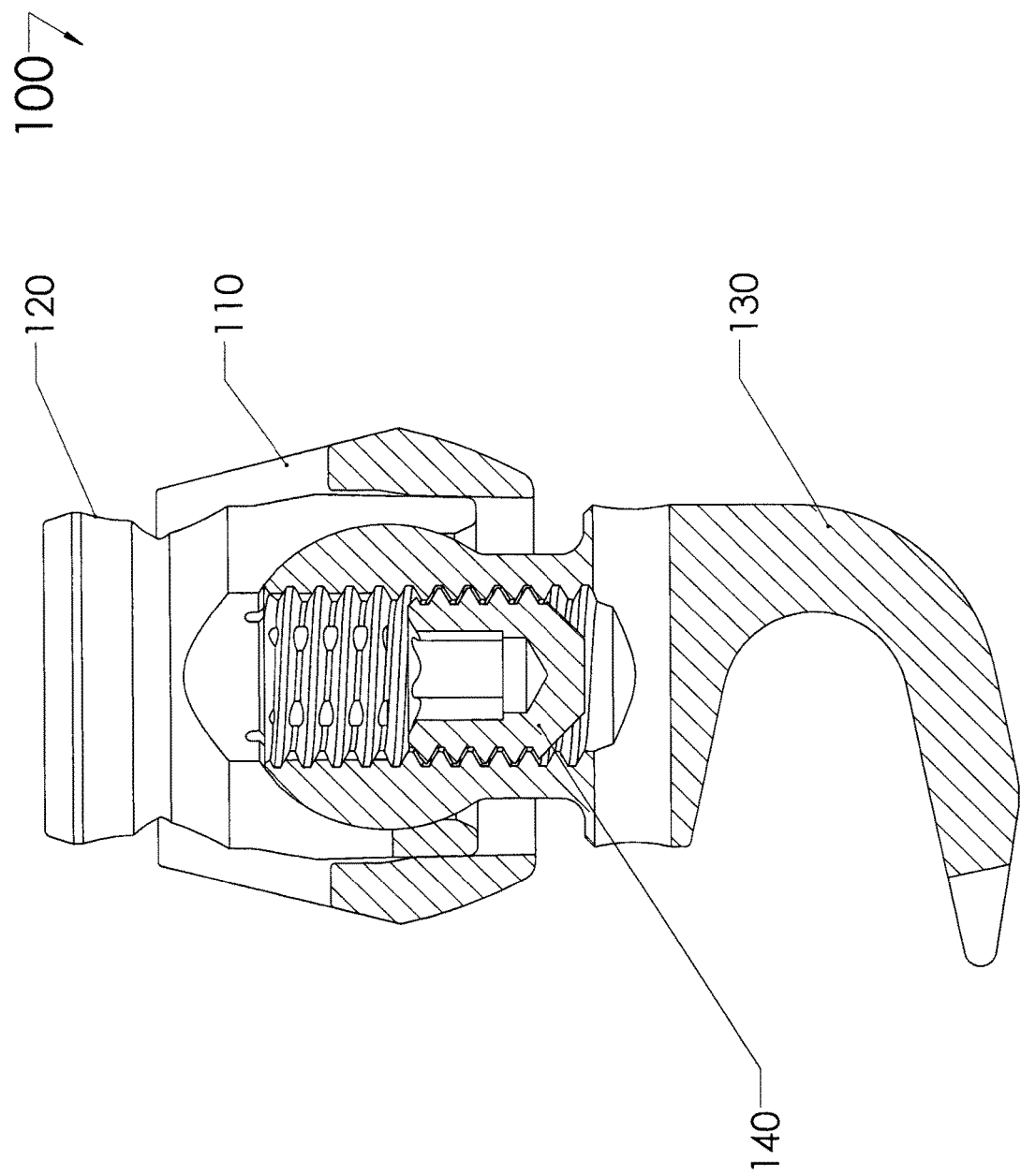
FIG. 4 is a cross-sectional view of the first hook assembly of FIG. 2 as taken along line 4-4 seen in FIG. 3.

Embodiments of the present disclosure are now described in detail with reference to the drawings in which like reference numerals designate identical or corresponding elements in each of the several views. As commonly known, the term "clinician" refers to a doctor, a nurse or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is known to indicate a direction toward a patient's head, whereas the term "caudal" indicates a direction toward the patient's feet. Further still, the term "lateral" is understood to indicate a direction toward a side of the body of the patient, i.e., away from the middle of the body of the patient. The term "posterior" indicates a direction toward the patient's back, and the term "anterior" indicates a direction toward the patient's front. Additionally, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

With reference to FIG. 1, one embodiment of a spinal stabilization assembly 1 includes a first hook assembly 100, a second hook assembly 200, and a spinal rod "R" that are configured to couple together for stabilizing a spine as described in greater detail below.

Turning now to FIGS. 2-14, the first hook assembly 100 of the spinal stabilization assembly 1 (FIG. 1) generally includes a receiver 105 having an outer housing 110 and an inner housing 120. The outer and inner housings 110, 120 of the receiver 105 together define a rod-receiving slot 105a of the receiver 105. The outer and inner housings 110, 120 have a taper lock arrangement so that the outer housing 110 slides over the inner housing 120 to releasably secure the spinal rod "R" (FIG. 1) within the rod-receiving slot 105a of the receiver 105. The first hook assembly 100 further includes a hook member 130 extending distally from the receiver 105. The first hook assembly 100 further includes a set screw 140 that threadably couples to the hook member 130 for coupling the first and second hook assemblies 100, 200 together and a pin 150 that couples the outer and inner housings 110, 120 together.

With reference to FIGS. 6-9, the outer housing 110 of the receiver 105 defines a central opening 110a therethrough configured to receive the inner housing 120 therein. The outer housing 110 further defines a pair of diametrically opposed openings 112a, 112b configured to accommodate the spinal rod "R" (FIG. 1). The outer housing 110 includes lips 114a, 114b, 114c, 114d that extend radially outward from the outer housing 110. The lips 114a-114d are configured to engage an instrument (not shown) for sliding the outer housing 110 relative to the inner housing 120 to selectively lock/unlock the spinal rod "R" to the receiver 105. The outer housing 110 further defines a bore 116a configured to receive the pin 150 for coupling the inner and outer housings 110, 120 together such that the outer and inner housings 110, 100 remain rotationally aligned. The outer housing 110 includes a tapered feature 118 defined by an inner surface of the outer housing 110 to facilitate taper lock engagement between the outer and inner housings 110, 120.

Figure 5:
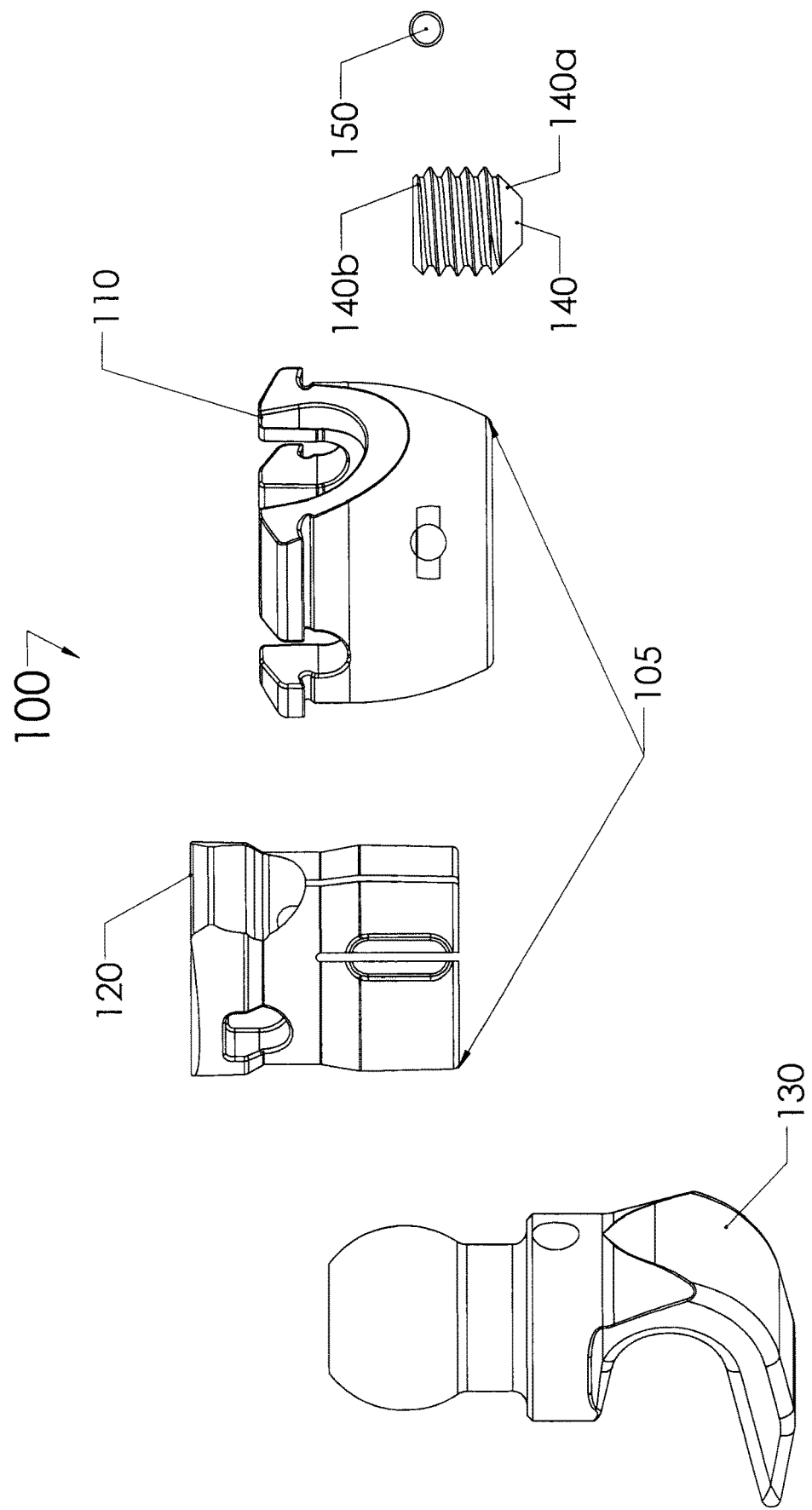
FIG. 5 is a perspective view, with parts separated, of the first hook assembly of FIG. 2.
Figure 6:
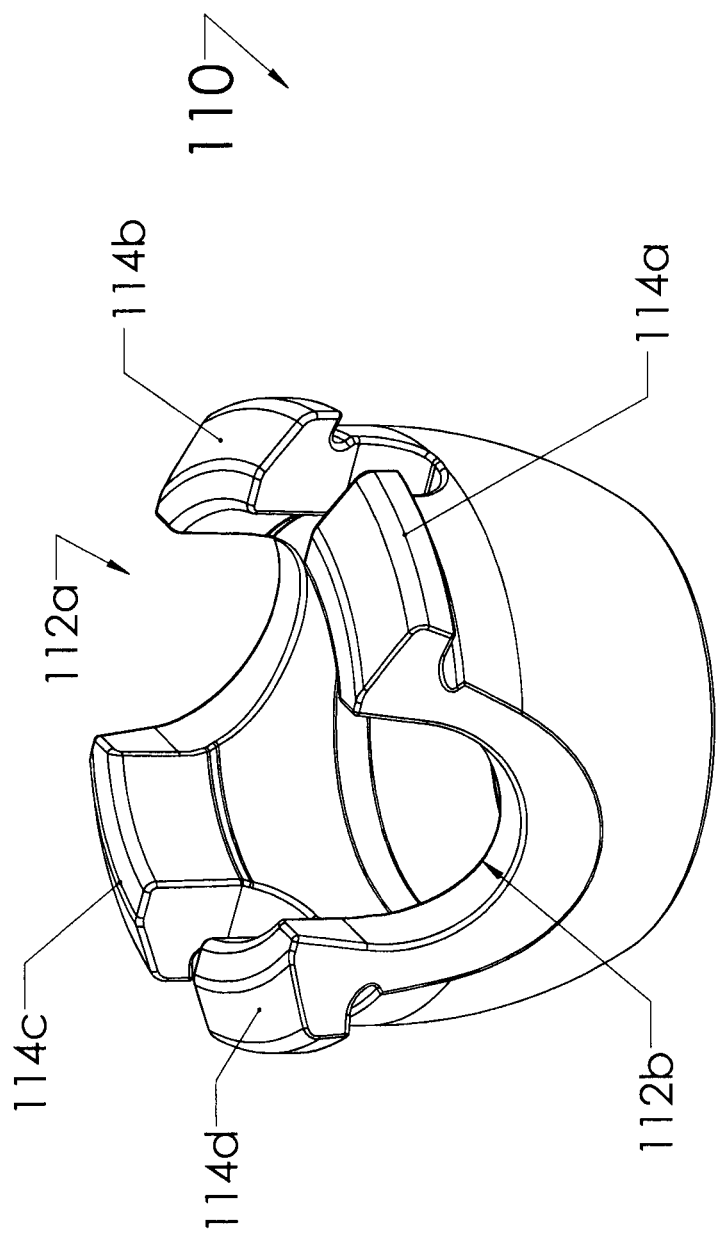
FIG. 6 is a perspective view of an outer housing of the first hook assembly of FIG. 2.
Figure 7:
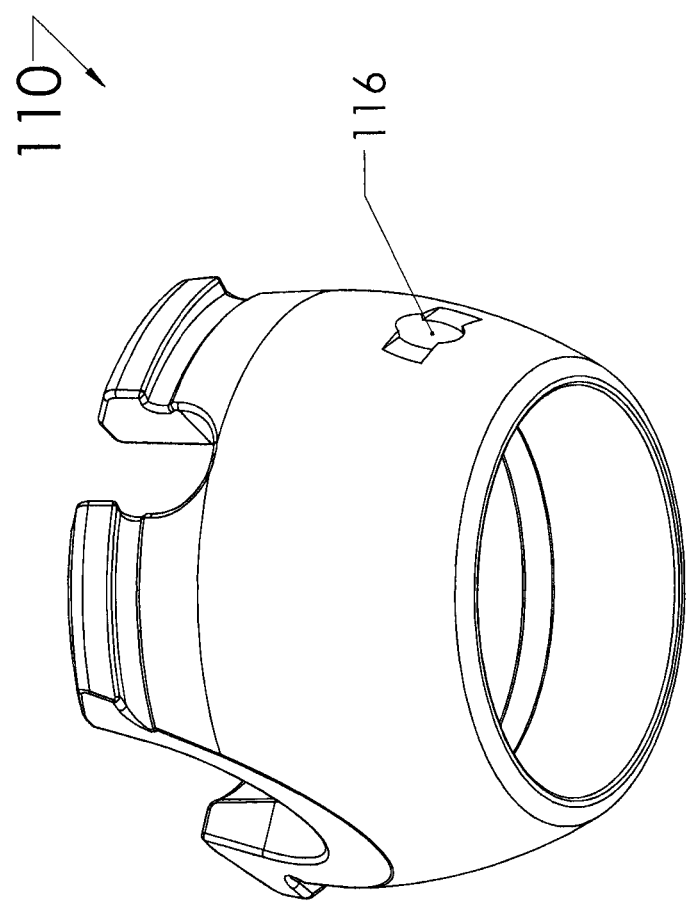
FIG. 7 is a bottom, perspective view of the outer housing of FIG. 6.
Figure 8:
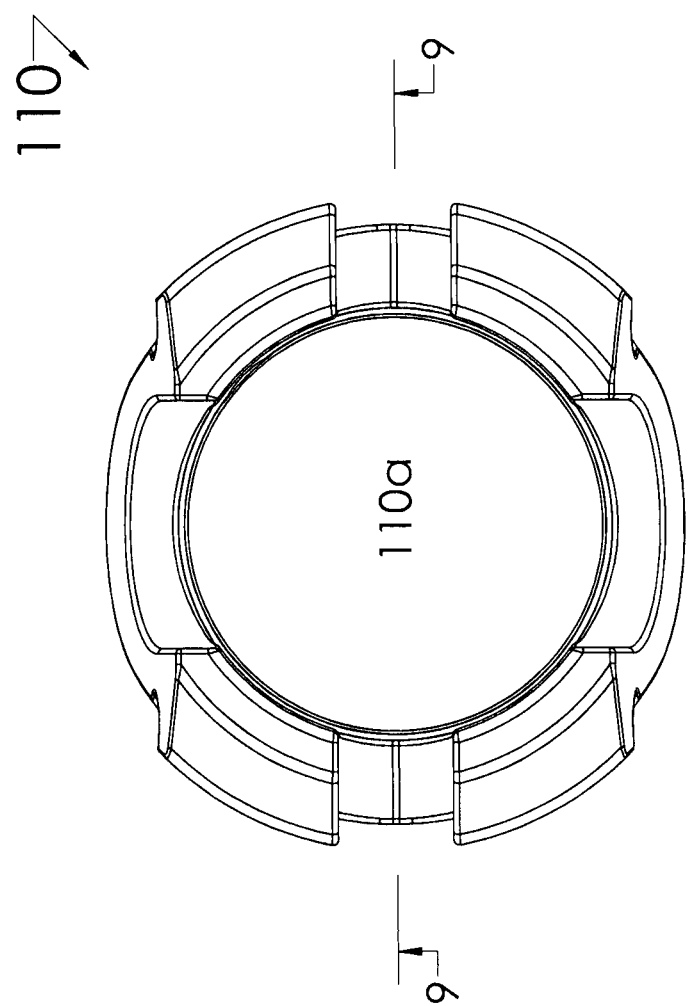
FIG. 8 is a top view of the outer housing of FIG. 6.
Figure 9:
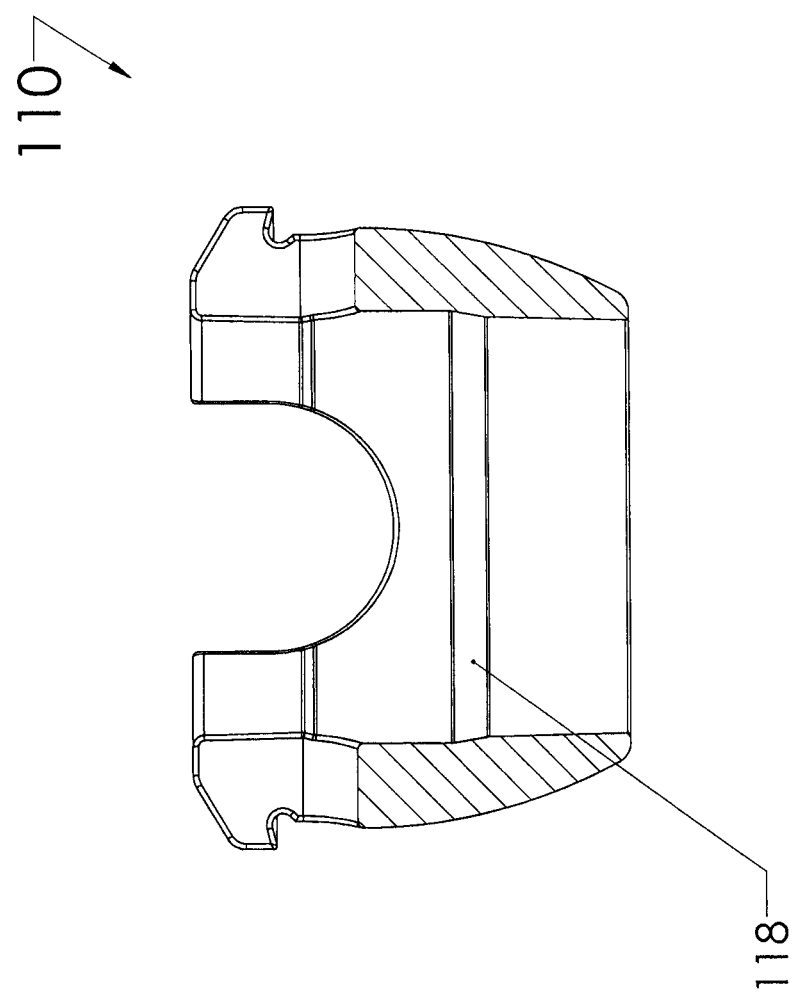
FIG. 9 is a cross-sectional view of the outer housing of FIG. 6 as taken along line 9-9 seen in FIG. 8.
Figure 10:
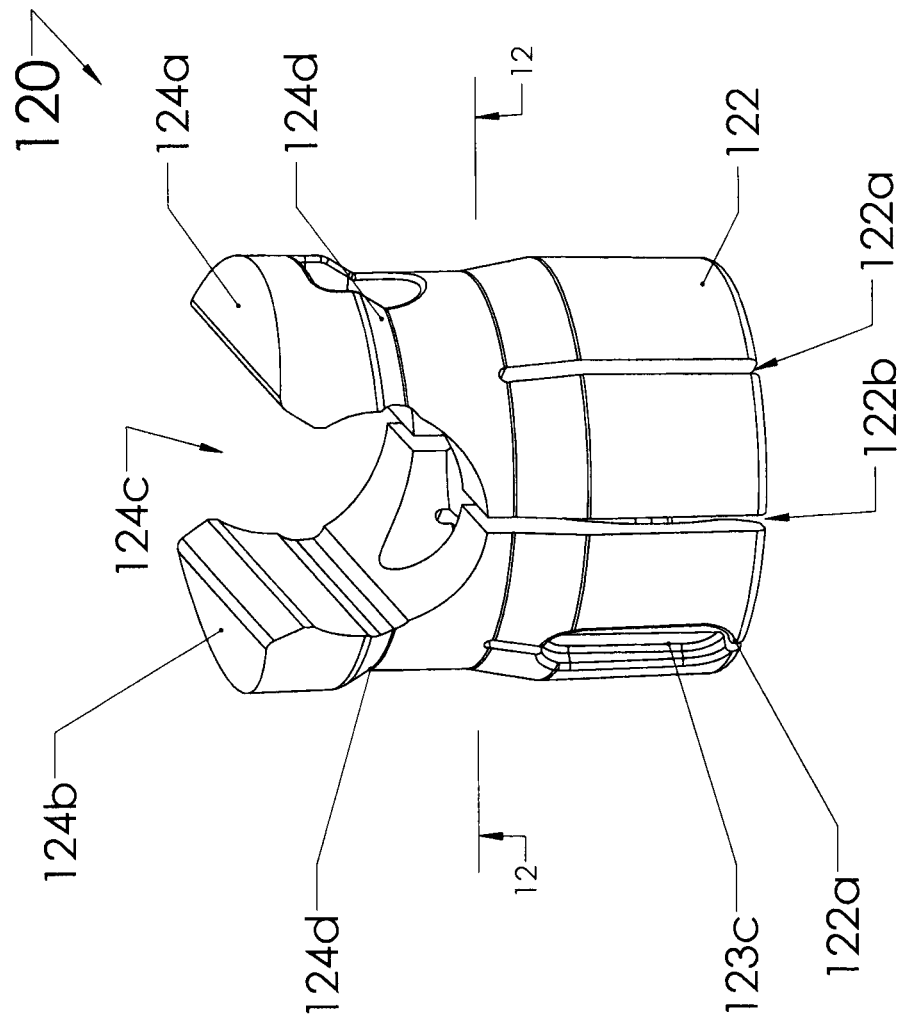
FIG. 10 is a perspective view of an inner housing of the first hook assembly of FIG. 2.
Figure 11:
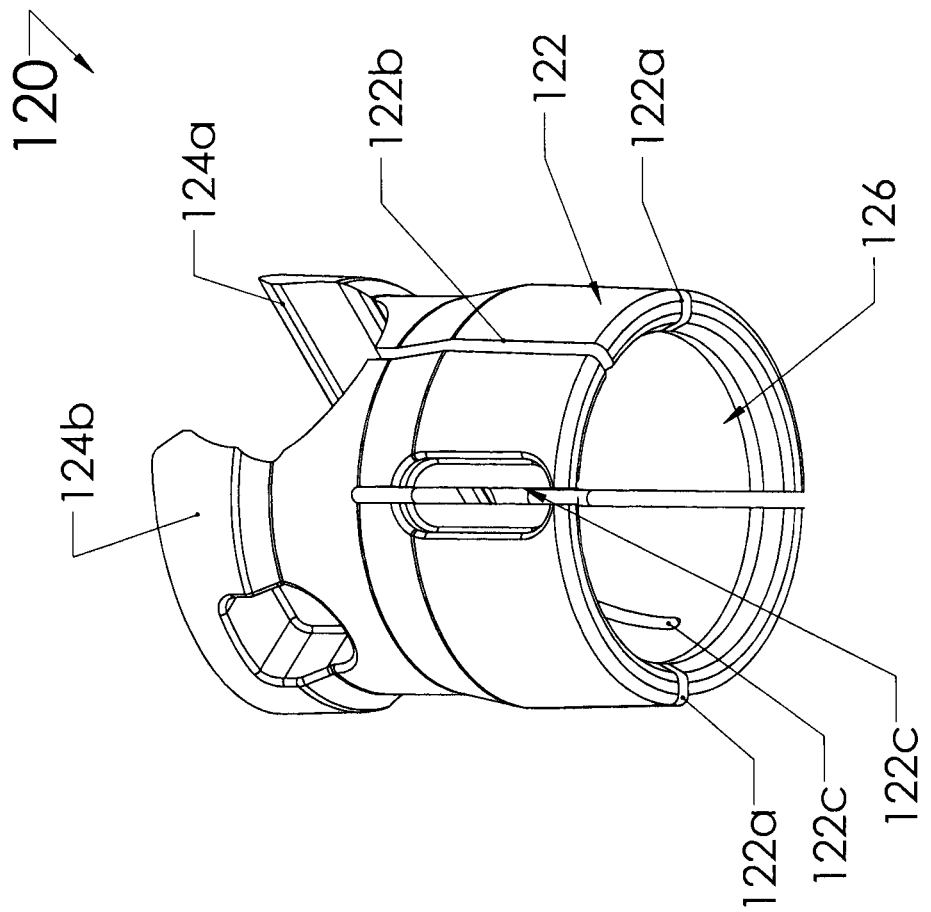
FIG. 11 is a bottom, perspective view of the inner housing of FIG. 10.
Figure 12:
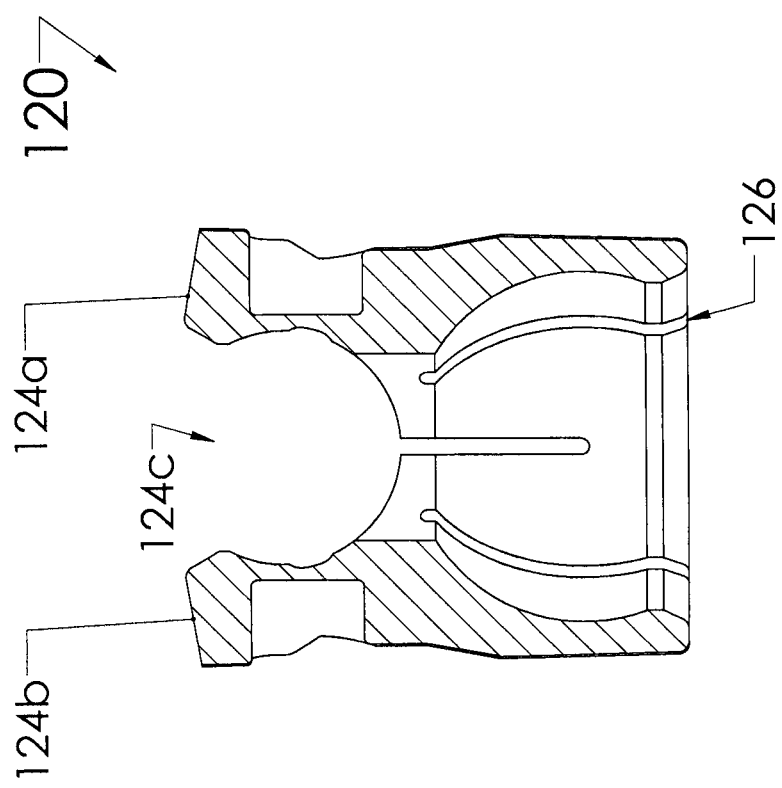
FIG. 12 is a cross-sectional view of the inner housing of FIG. 10 as taken along line 12-12 of FIG. 10.

Referring to FIGS. 10-12, the inner housing 120 of the receiver 105, which may be in the form of a collet, includes a base 122 and a pair of arms 124a, 124b extending proximally from the base 122. The arms 124a, 124b of the inner housing 120 define a slot 124c between the arms 124a, 124b that is configured to receive the spinal rod "R" (FIG. 1) The slot 124c of the inner housing 120 may be U-shaped. Each of the arms 124a, 124b of the inner housing 120 includes a tapered surface 124d configured to selectively engage the inner surface of outer housing 110 to selectively lock the inner and housings 110, 120 together. The base 122 of the inner housing 120 is generally cylindrical and defines a recess 126 that receives a portion of the hook member 130 of the first hook assembly 100 within the recess 126 of the inner housing 120. The recess 126 may have a spherical configuration. The base 122 of the inner housing 120 defines a slits 122a, 122b, 122c, etc. configured to enable radial deflection of the base 122 so that the hook member 130 of the first hook assembly 100 can be received and retained within the recess 126 of the inner housing 120. The base 122 also defines a slot 123 configured to slidably receive the pin 150 (FIG. 5).

Figure 13:
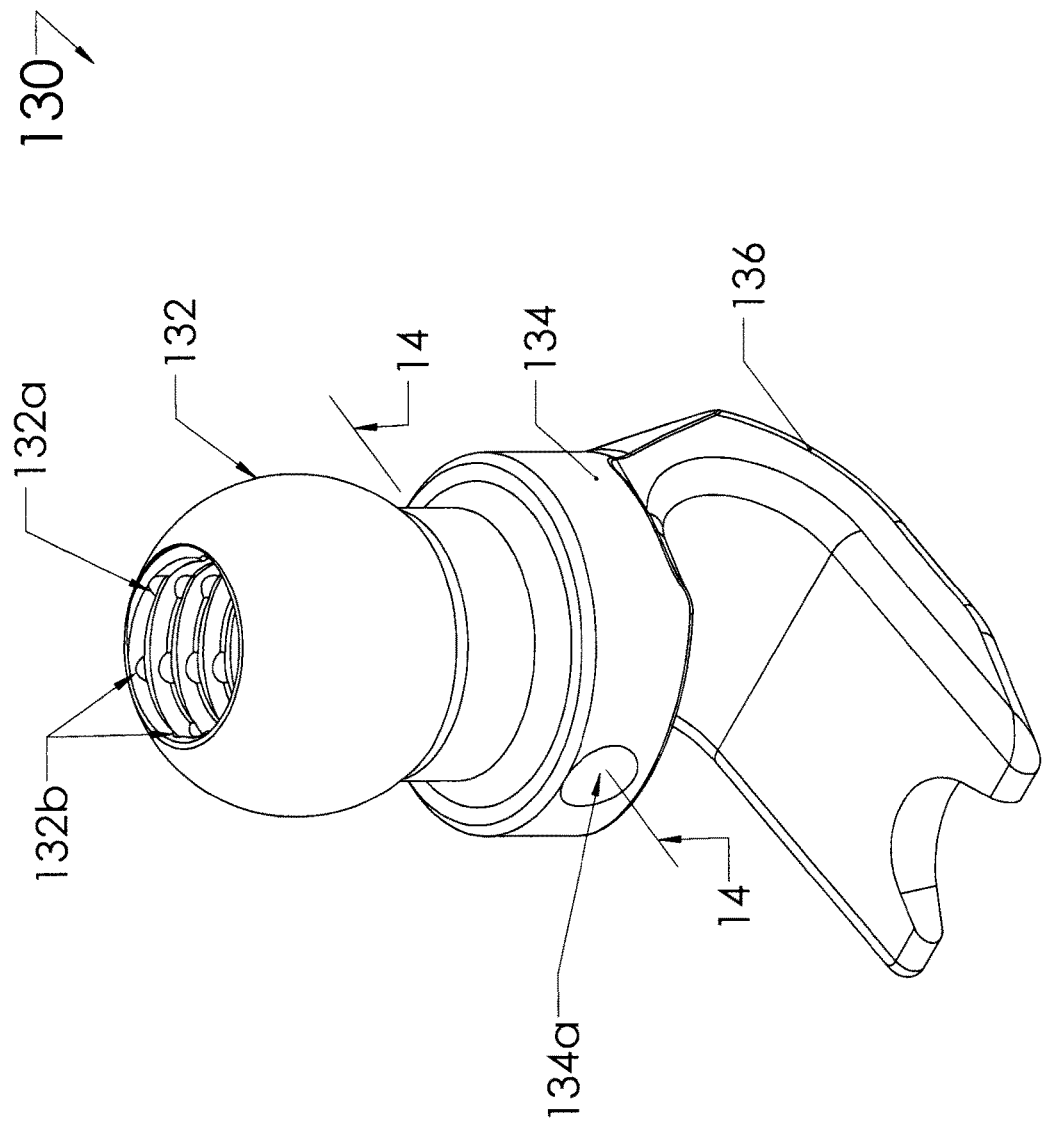
FIG. 13 is a perspective view of a hook member of the first hook assembly of FIG. 2.
Figure 14:
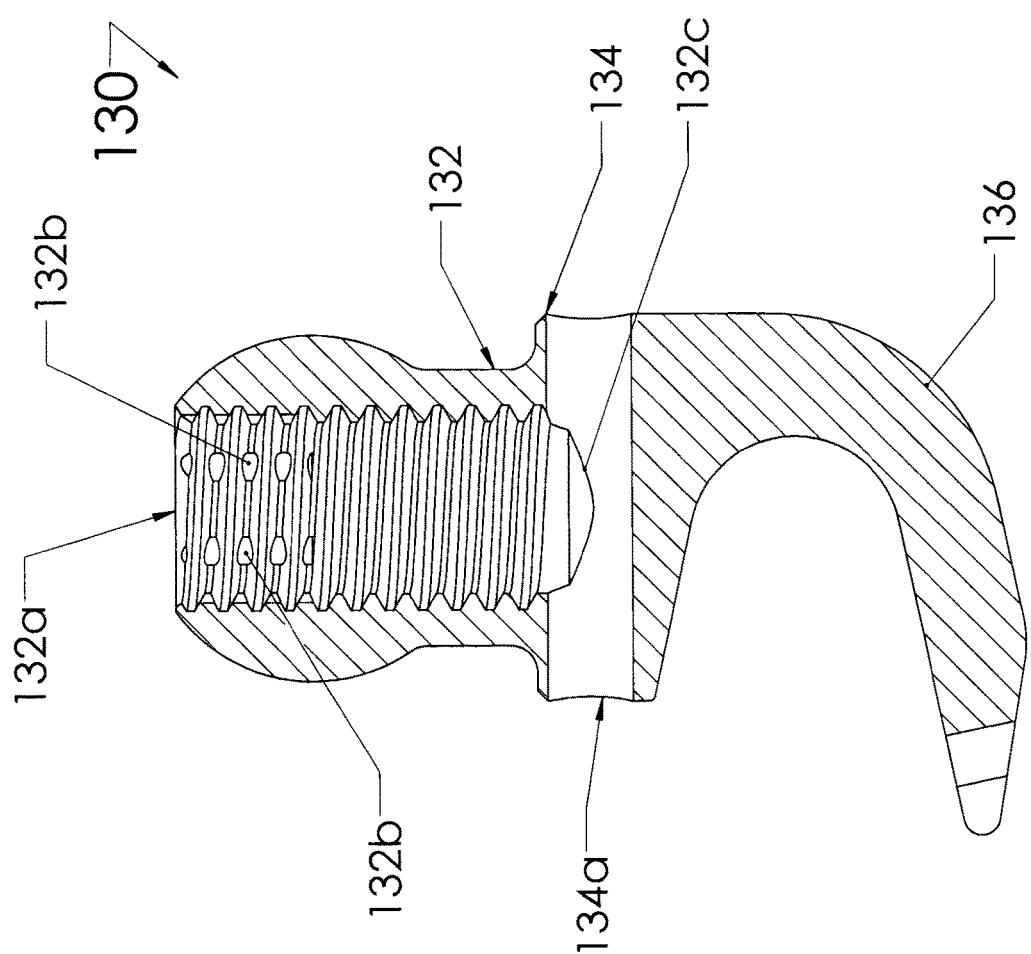
FIG. 14 is a side cross-sectional view of the hook member of FIG. 13 as taken along line 14-14 seen in FIG. 13.
Figure 15:
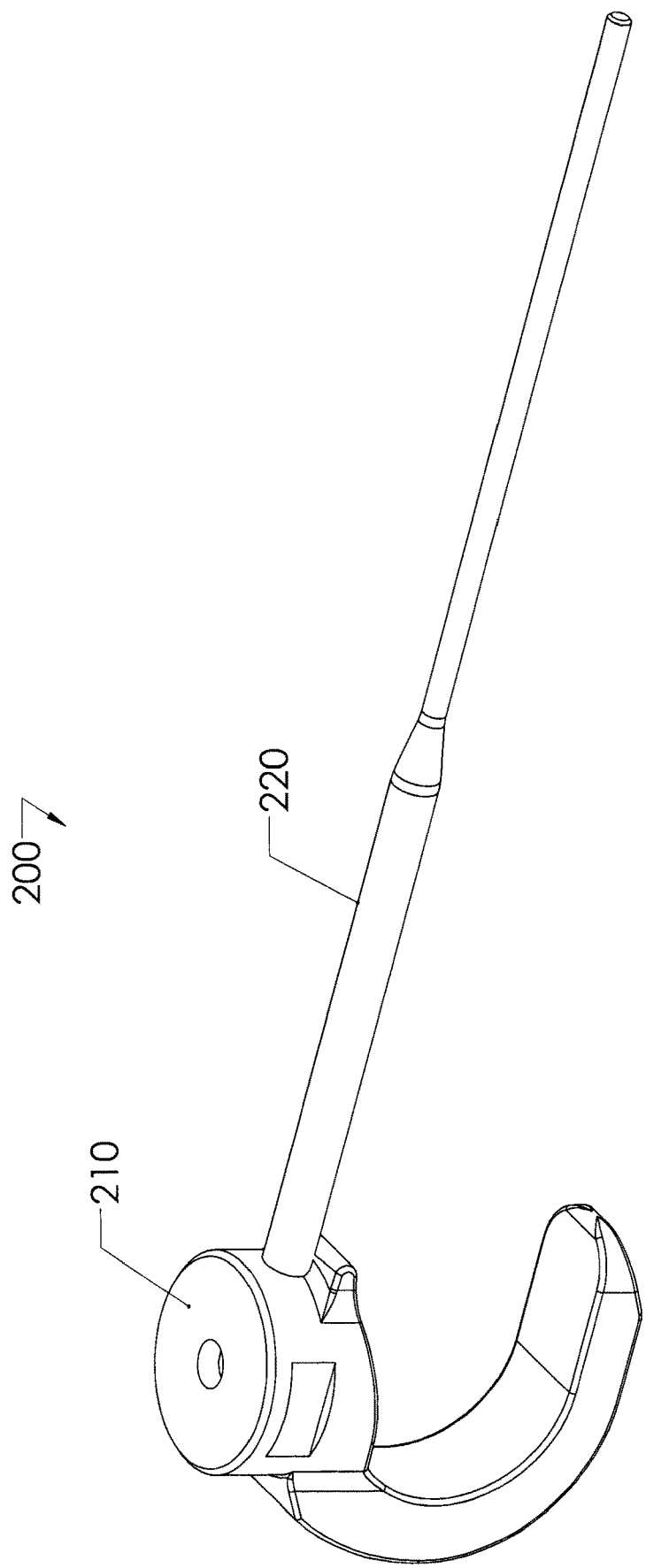
FIG. 15 is a perspective view of a second hook assembly of the spinal stabilization assembly of FIG. 1.
Figure 16:
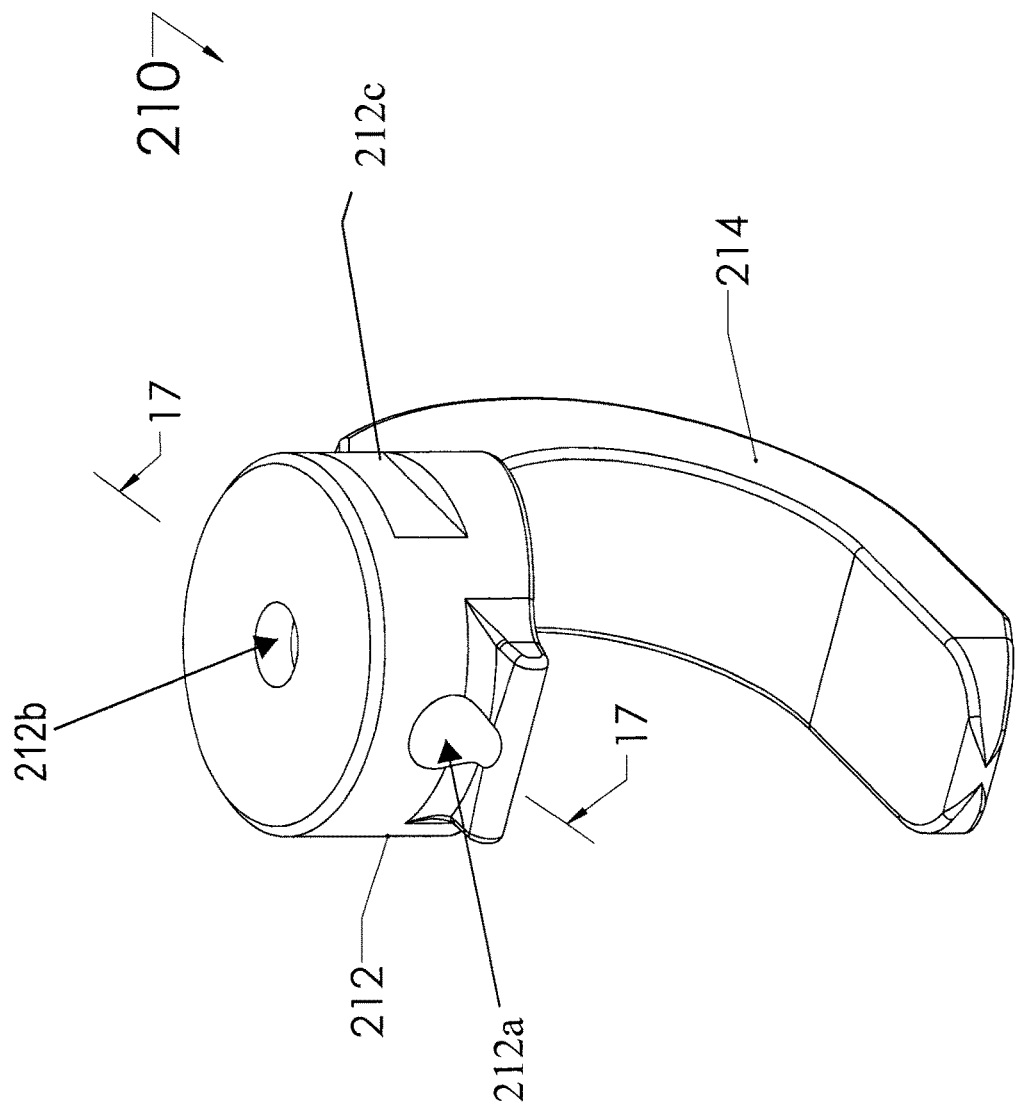
FIG. 16 is a perspective view of a hook member of the second hook assembly of FIG. 15.
Figure 17:
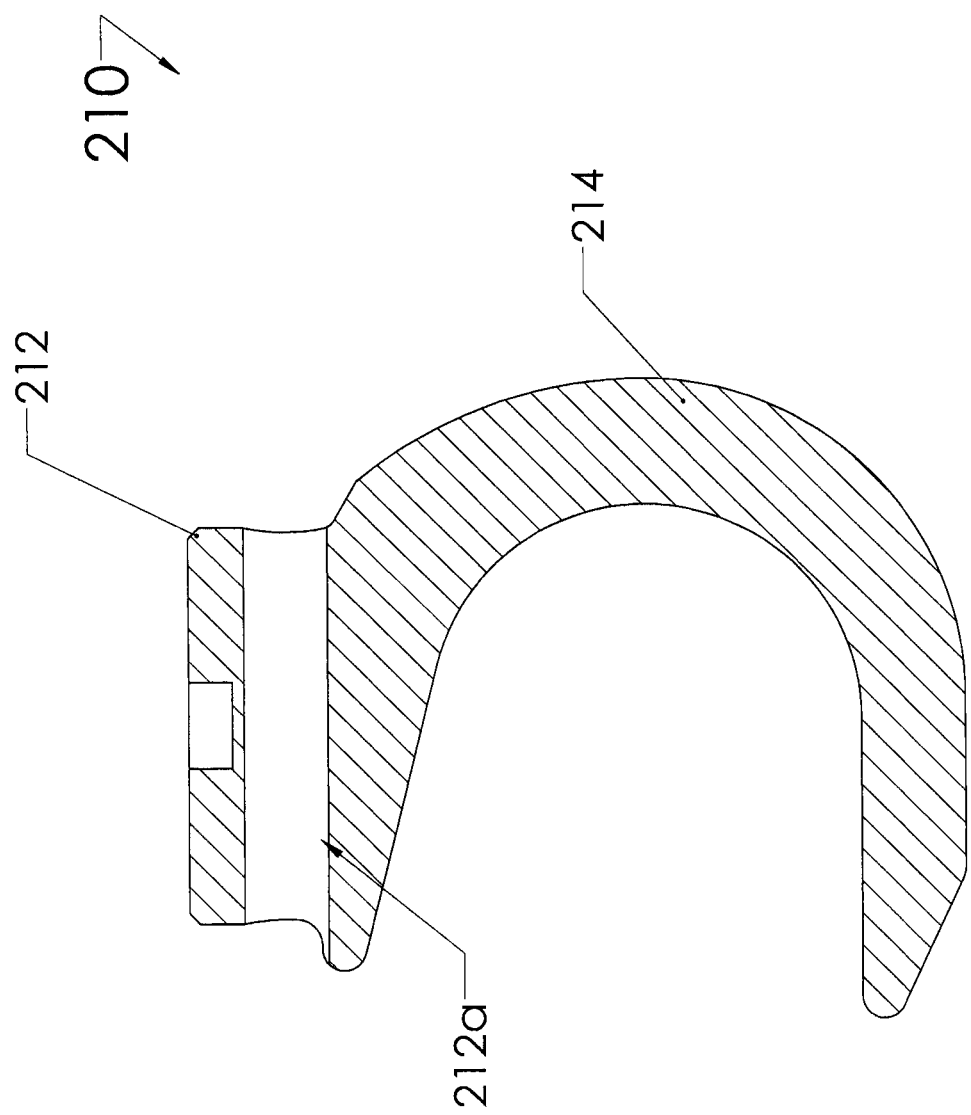
FIG. 17 is a side cross-sectional view of the hook member of FIG. 16 as taken along line 17-17 seen in FIG. 16.
Figure 18:
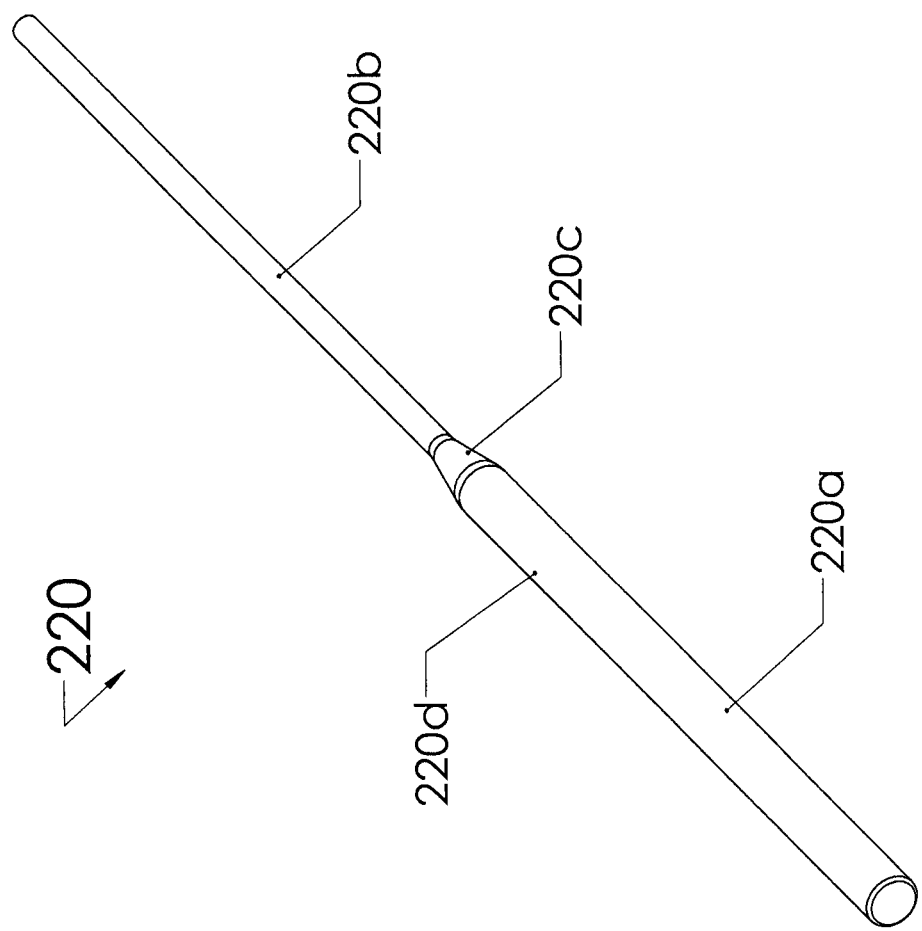
FIG. 18 is a perspective view of a connector member of the second hook assembly of FIG. 15.

With reference to FIGS. 13 and 14, the hook member 130 of the first hook assembly 100 includes a head 132, a coupling member 134 supporting the head 132, and a hook 136 extending distally from the coupling member 134. The head 132 of the hook member 130 may include a spherical configuration. The head 132 defines a threaded opening 132a therethrough that is configured to threadably engage the set screw 140 (FIG. 5) of the first hook assembly 100 therein. The threaded opening 132a of the head 132 includes notches 132b at spaced apart locations about the threaded opening 132a. The notches 132b are configured to mate with an insertion instrument (not shown) for effectuating insertion. The coupling member 134 of the hook member 130 defines an aperture 134a therethrough and defines a distal tip portion 132c of the threaded opening 132a. The aperture 134a of the coupling member 134 is in communication with the threaded opening 132a of the head 132. A distal tip portion 140a of the set screw 140 (FIG. 5) of the first hook assembly 100 is positionable within the aperture 134a of the coupling member 134 while a proximal portion 140b of the set screw 140 is disposed in the threaded opening 132a of the head 132 of the hook member 130. The hook 136 is configured to anchor to bone, for example, to an undersurface of a lamina of the spine.

For a detailed discussion of similar hook assemblies, of which one or more components thereof can be utilized in connection with, and/or modified for use with, the presently disclosed spinal stabilization assemblies, reference can be made to U.S. Pat. App. Pub. No. 2014/0277155, filed Mar. 14, 2014, and U.S. Pat. App. Pub. No. 2015/0230828, filed Feb. 20, 2014, the entire contents of each of which are incorporated by reference herein.

Turning now to FIGS. 15-18, the second hook assembly 200 of the spinal stabilization assembly 1 generally includes a hook member 210 and a connector member 220 extending from the hook member 210.

The hook member 210 includes a head 212 and a hook 214 that extends distally from the head 212. The hook 214 of the hook member 210 is configured to anchor to bone, for example, to an undersurface of a lamina of the spine. The head 212 defines an aperture 212a therethrough that receives a proximal end portion 220a of the connector member 220 so that a distal end portion 220b of the connector member 220 extends from the head 212 in a cantilevered manner. The head 212 further defines a top bore 212b therein and side channels 212c (only one being shown in FIG. 16 with the other being disposed on the opposite side of the head 212 in mirrored relation thereto). The top bore 212b and 212c are mating features that function to be engaged by an insertion instrument (not shown) for effectuating insertion. The proximal end portion 220a of the connector member 220 may be secured to the head 212 using known fastening techniques such as welding, adhering, fastening, etc. The distal end portion 220b of the connector member 220 is coupled to the proximal end portion 220a of the connector member 220 by a transition portion 220c of the connector member 220 that tapers distally to the distal end portion 220b.

In use, with reference to FIGS. 1-18, the hooks 136, 214 of the respective first and second hook assemblies 100, 200 are mountable to one or more spinal bones (e.g., lamina). The distal end portion 220b of the connector member 220b is slidably receivable within the aperture 134a of the first hook assembly 100 to couple the first and second hook assemblies 100, 200 together and to enable relative movement between the first and second hook assemblies 100, 200 between a first position and one or more second positions (e.g., a multitude of different positions). Relative approximating movement between the first and second hook assemblies 100, 200 shortens a distance between the hooks 136, 124 of the respective first and second hook assemblies 100, 200, for example, to clamp two or more spinal bones together. Relative unapproximating movement between the first and second hook assemblies 100, 200 lengthens a distance between the hooks 136, 214 of the respective first and second hook assemblies 100, 200. The first and/or second hook assemblies 100, 200 can be manipulated (e.g., approximated and/or unapproximated) as desired until the hooks 136, 214 of the respective first and second hook assemblies 100, 200 are positioned at a desired distance from one another, for example, to achieve a clamping effect on the spinal bones secured between the first and second hook assemblies 100.

Once the hooks 136, 214 of the respective first and second hook assemblies 100, 200 are positioned at the desired distance from one another, the set screw 140 can be advanced through the threaded opening 132a of the hook member 130 of the first hook assembly 100 so that the distal tip portion 140a of the set screw 140 contacts an outer surface 220d of the connector member 220 of the second hook assembly 200 to fix the hooks 136, 214 of the respective first and second hook assemblies 100, 200 at the desired distance from one another. The set screw 140 of the first hook assembly 100 can be tightened until frictional engagement between the outer surface 220d of the connector member 220 of the second hook assembly 200 and the distal tip portion 140a of the set screw 140 of the first hook assembly 100 prevent the connector member 220 of the second hook assembly 200 from sliding through the aperture 134a of the first hook assembly 100, fixing the distance between the hooks 136, 214 of the respective first and second hook assemblies 100, 200.

With the pin 150 of the first hook assembly 100 maintaining the outer and inner housings 110, 120 in rotational alignment with respect to one another, the outer and inner housings 110, 120 can be polyaxially manipulated about the hook member 130 of the first hook assembly 100 (e.g., via the spherical ball-joint configuration of the recess 126 of the inner housing 120 and the head 132 of the hook member 130) to achieve a desired angular orientation between the receiver 105 and the hook member 130 of the first hook assembly 100. Once the receiver 105 of the first hook assembly 100 is disposed at a desired angular orientation relative to the hook member 130 of the first hook assembly 100, the spinal rod "R" can be selectively fixed within the rod-receiving slot 105a of the receiver 105 by axially moving the outer housing 110 of the first hook assembly 100 relative to the inner housing 120 of the first hook assembly 100 to effectuate taper lock with the outer and inner housings 110, 120 of the receiver 105.

Figure 19:
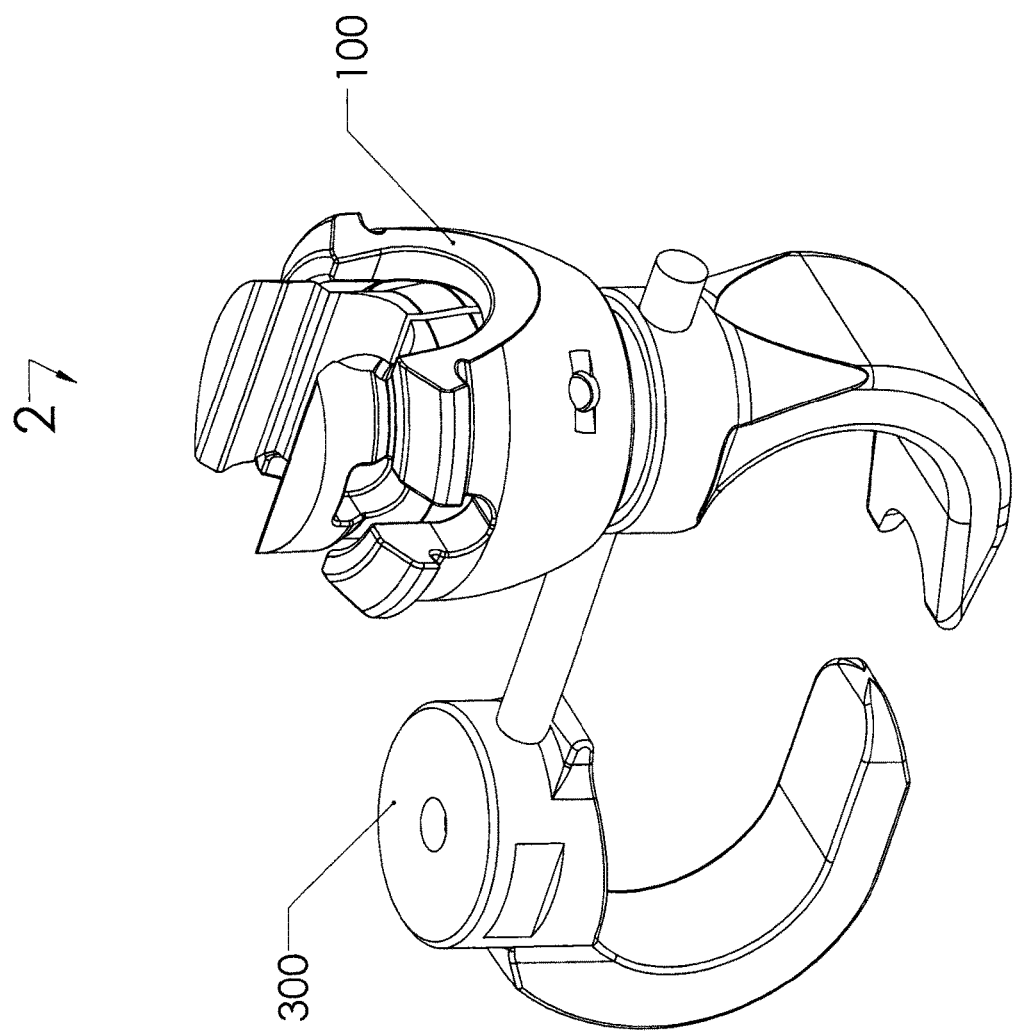
FIG. 19 is a perspective view of another embodiment of a spinal stabilization assembly in accordance with the principles of the present disclosure.
Figure 20:
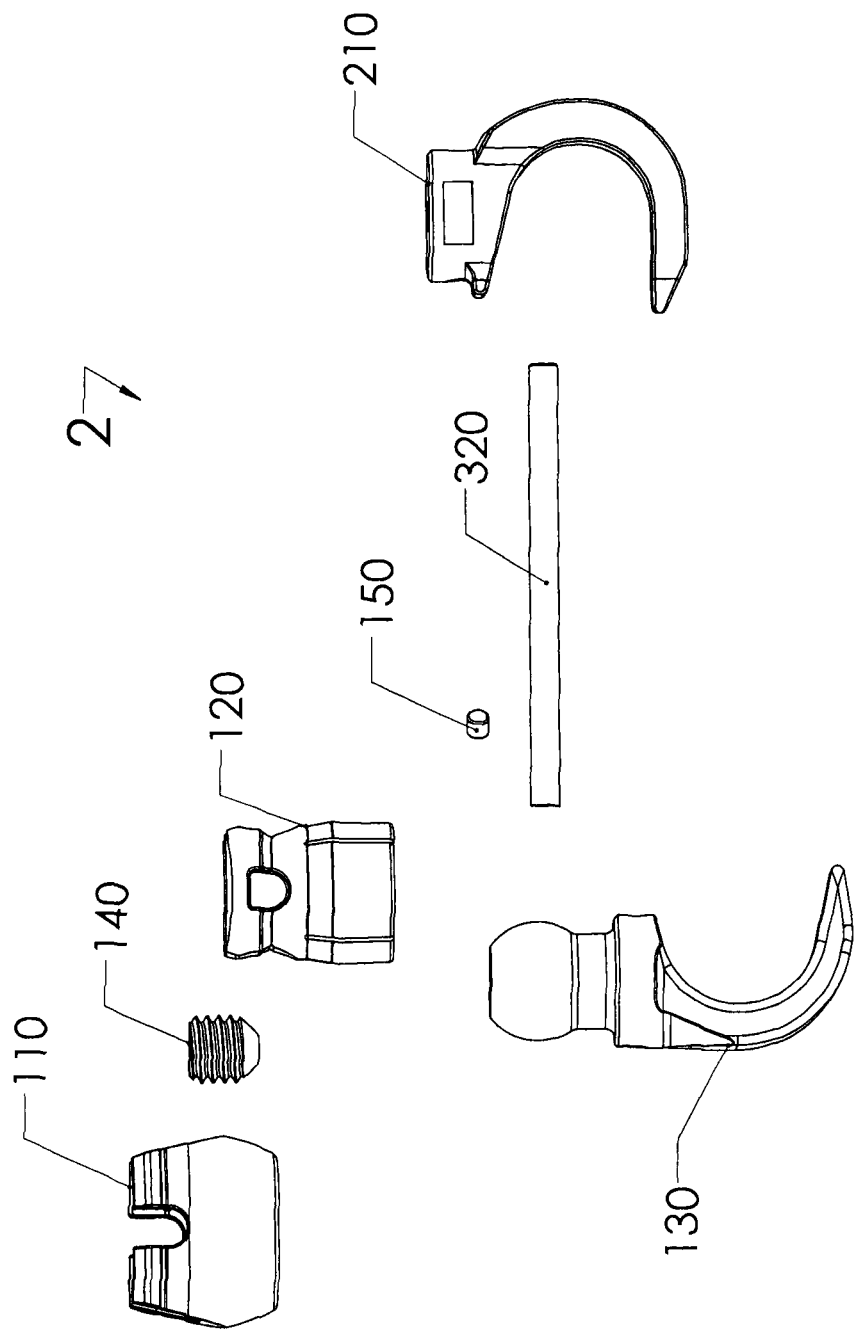
FIG. 20 is a side view, with parts separated, of the spinal stabilization assembly of FIG. 19.

Turning now to FIGS. 19 and 20, another embodiment of a spinal stabilization assembly, generally referred to as 2, includes a first hook assembly 100 and a second hook assembly 300. The second hook assembly 300 is similar to the second hook assembly 200 of the spinal stabilization assembly 1, but includes a connector member 320 having a uniform diameter along a length of the connector member 320.

Any of the presently disclosed embodiments, or components thereof, can be formed of any suitable material or combinations of materials such as mixed metallic materials like titanium alloy and cobalt-chromium.

Any of the presently disclosed embodiments, or components thereof can be formed using any suitable technique such as welding, fastening, machining, molding, etc. In some embodiments, one or more of the components can be secured together using any suitable technique such as welding, fastening, machining, molding, etc. Any of the components may be press-fit together.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A spinal stabilization assembly comprising:
    a first hook assembly having a receiver and a hook member extending from the receiver, the receiver including an outer housing and an inner housing supported within the outer housing, the inner and outer housings defining a rod-receiving slot configured to receive a spinal rod therein, the hook member including a head supported on a trailing end thereof, the inner housing being supported on the head, and the hook member including a hook and including a coupling member supported between the head and the hook, the hook member defining an aperture positioned through the coupling member between the rod-receiving slot and the hook;
    a second hook assembly; and
    a connector member that is secured to the second hook assembly and is at least partially receivable in the aperture of the first hook assembly to couple the first and second hook assemblies together;
    wherein the inner and outer housings are supported in a taper lock arrangement configured such that relative movement between the inner and outer housings causes the inner housing to selectively clamp the spinal rod within the rod-receiving slot; and
    wherein the first hook assembly includes a set screw receivable within the receiver of the first hook assembly, the set screw being selectively positionable in contact with the connector member to fix a distance between the first and second hook assemblies.

2. The spinal stabilization assembly of claim 1, wherein at least a portion of the connector member is slidably received in the aperture to selectively position the first and second hook assemblies between first and second positions, wherein in the second position, the first and second hook assemblies are closer to one another than in the first position.

3. The spinal stabilization assembly of claim 1, wherein the second hook assembly includes a hook, wherein the hooks of the first and second assemblies are disposed in mirrored relation with one another and in parallel relation with the connector member.

4. The spinal stabilization assembly of claim 1, wherein the second hook assembly is supported entirely beneath the spinal rod while the spinal rod is secured within the rod-receiving slot of the first hook assembly.

5. The spinal stabilization assembly of claim 1, wherein the receiver and the hook member of the first hook assembly are polyaxially movable relative to one another.

6. A spinal stabilization assembly comprising:
    a spinal rod;
    a first hook assembly having a receiver and a hook member extending from the receiver, the receiver including an outer housing and an inner housing supported within the outer housing, the inner and outer housings defining a rod-receiving slot configured to receive the spinal rod therein, the hook member including a head supported on a trailing end thereof, the inner housing being supported on the head, and the hook member including a hook and including a coupling member supported between the head and the hook;
    a second hook assembly; and
    a connector member that extends between the first and second hook assemblies, the connector member secured to the first assembly and selectively securable to the second hook assembly;
    wherein the inner and outer housings are supported in a taper lock arrangement configured such that relative movement between the inner and outer housings causes the inner housing to selectively clamp the spinal rod within the rod-receiving slot; and wherein the coupling member defines an aperture that is positioned to receive the connector member therethrough; and
    wherein the first hook assembly includes a set screw receivable within the receiver of the first hook assembly, the set screw being selectively positionable in contact with the connector member to fix a distance between the first and second hook assemblies.

7. The spinal stabilization assembly of claim 6, wherein the connector member is slidably received through the first hook assembly.

8. The spinal stabilization assembly of claim 6, wherein the second hook assembly includes a hook member, wherein the hook members of the first and second assemblies are disposed in mirrored relation with one another and in parallel relation with the connector member.

9. The spinal stabilization assembly of claim 6, wherein the second hook assembly is supported entirely beneath the spinal rod while the spinal rod is secured within the rod-receiving slot of the first hook assembly.

10. A method for stabilizing a spine, the method comprising:

securing a hook of a first hook assembly to a first spinal bone, the first hook assembly having a receiver and a hook member extending from the receiver, the receiver including an outer housing and an inner housing supported within the outer housing, the inner housing being supported on a head of the hook member, and the hook member including the hook and including a coupling member supported between the head and the hook;

securing a hook of second hook assembly to a second spinal bone;

coupling a connector member of the second hook assembly to the first hook assembly by positioning the connector member through an aperture defined in the coupling member between the rod-receiving slot and the hook;

adjusting a distance between the first and second hook assemblies to manipulate the first and second spinal bones relative to one another;

securing the connector member of the second hook assembly to the first hook assembly to fix a distance between the first and second hook assemblies; and securing a spinal rod to the receiver of the first hook assembly by moving the outer housing of the receiver relative to the inner housing of the receiver to cause the inner housing to clamp the spinal rod within a rod-receiving slot defined by the inner and outer housings of the receiver.

11. The method of claim 10, wherein the step of adjusting a distance between the first and second hook assemblies comprises sliding the connector member through the aperture of the first hook assembly.

12. The method of claim 10, wherein the step of securing the connector member of the second hook assembly to the first hook assembly comprises advancing a set screw within the receiver of the first hook assembly and into contact with the connector member.

13. The method of claim 10, further comprising polyaxially pivoting the receiver of the first hook assembly relative to the hook of the first hook assembly before clamping the spinal rod within the rod-receiving slot.

\* \* \* \* \*